| United States Patent [19] | [11] Patent Number: 4,918,009 |
| Nilsson | [45] Date of Patent: Apr. 17, 1990 |

[54] METHOD OF CONTROLLING THE REGIOSELECTIVITY OF GLYCOSIDIC BONDS

[75] Inventor: Kurt G. I. Nilsson, Lund, Sweden

[73] Assignee: Svenska Sockerfabriks AB, Malmo, Sweden

[21] Appl. No.: 938,703

[22] Filed: Dec. 4, 1986

[30] Foreign Application Priority Data

Dec. 11, 1985 [SE] Sweden ................ 8505842

[51] Int. Cl.$^4$ .................. C12P 19/64; C12N 9/24
[52] U.S. Cl. ........................ 435/73; 435/96;
435/18; 435/22; 435/74; 435/85; 435/98;
435/200; 435/201; 435/207; 435/208; 536/4.1;
536/17.4; 536/17.6
[58] Field of Search ............ 435/15, 18, 22, 73,
435/74, 84, 85, 96, 97, 176, 195, 200, 201, 207,
208; 536/4.1, 17.4, 17.6

[56] References Cited

U.S. PATENT DOCUMENTS

| 4,225,672 | 9/1980 | Hall .................... 435/74 |
| 4,544,631 | 10/1985 | Rauscher et al. ........ 435/14 |
| 4,675,392 | 6/1987 | Dahmen et al. ......... 526/17.6 |
| 4,762,917 | 8/1988 | Ikenaka et al. ......... 536/4.1 |

OTHER PUBLICATIONS

Enzyme Nomenclature, Academic Press, New York (1979) pp. 274–294.
Chang, T. M. S., "Microencapsulation of Enzymes and Biologicals", in *Methods in Enzymology* vol XLIV, (1976) pp. 201–203, 211–213.

*Primary Examiner*—Robert Wax
*Assistant Examiner*—Mary E. Pratt
*Attorney, Agent, or Firm*—Beveridge, DeGrandi & Weilacher

[57] ABSTRACT

A method of controlling the regioselectivity of the glycosidic bond between glycosyl donor and glycosyl acceptor in the enzymatic production of an oligosaccharide compound which either consists of or is a fragment or an analog of the cabohydrate part in a glycoconjugate, by reverse hydrolysis or transglycosidation reactions, is described. The synthesis is carried out in that a donor substance which is a mono- or oligosaccharide or a glycoside thereof, is caused to react, in the presence of a glycosidase, with an acceptor substance which is an O-, N-, C- or S-glycoside consisting of a monosaccharide, oligosaccharide or a saccharide analog and at least one aglycon which is O-, N-, C- or S-glycosidically bonded in 1-position, the $\alpha$ or $\beta$-configuration being selected on the glycoside bond between the glycosyl group and the aglycon in the acceptor substance, and the oligosaccharide compound being separated from the reaction mixture.

23 Claims, No Drawings

METHOD OF CONTROLLING THE REGIOSELECTIVITY OF GLYCOSIDIC BONDS

The present invention relates to a method of controlling the regioselectivity of the glycosidic bond formed between glycosyl donor and glycosyl acceptor in the enzymatic production of an oligosaccharide compound which either consists of or is a fragment or an analog of the carbohydrate part in a glycoconjugate, by reverse hydrolysis or transglycosidation. Furthermore, the invention relates to the use of the product prepared by this method.

It has been found in recent years that the oligosaccharide part of various glycoconjugates (especially glycoproteins and glycolipids) exercises a number of important functions in vivo (Biology of Carbohydrates, Vol. 2, Ginsburg et al, Wiley, N.Y. (1984); S. Hakomori, Ann. Rev. Biochem., Vol. 50, pp. 733–64). Among other things, it was found that the carbohydrate structures are important to the stability, activity, localisation and degradation of glycoproteins;

certain oligosaccharide structures activate plant secretion of antimicrobial substances;

the glycoconjugates are frequently found on the surfaces of various cells and are important, inter alia, to cell interaction with the surroundings since they function as receptors or regulators when bonded to cell surfaces of, for example, peptides, hormones, toxins, viruses, bacteria and during cell-cell interaction;

are antigenic determinants (for example blood group antigen);

function as cell differentiating antigen during normal tissue development;

are important to oncogenesis since specific oligosaccharides have been found to be cancer-associated antigenic determinants;

are important to sperm/egg interaction and to fertilisation.

A large number of oligosaccharide structures comprised by various glycoconjugates have today been verified, and also the minutest unit (frequently a di- or trisaccharide) necessary for the biological activity of a known oligosaccharide has in many cases been determined. As a consequence, universities and industry are at present working intensely on developing the use of biologically active oligosaccharides within a number of different fields, such as the development of novel diagnostics and blood typing reagents;

the synthesis of highly specific materials for affinity chromatography;

the development of monoclonal antibodies;

the production of cell specific agglutination reagents;

the development of novel therapeutical techniques by means of so-called drug targeting where use is made of microspheres (<1 micrometers) enclosing a drug and carrying on the surface of the microsphere a specific oligosaccharide;

the development of a novel type of therapy as an alternative to antibiotics, based on the inhibition of the adhesion of bacteria and viruses to cell surfaces by means of specific oligosaccharides;

the stimulation of plant growth and protection against pathogens.

Besides the above-mentioned fields, a considerable future market is envisaged for fine chemicals based on biologically active carbohydrates.

Only some ten different monosaccharides are included in the carbohydrate part of the glycoconjugates, viz. D-glucose (Glc), D-galactose (Gal), D-mannose (Man), L-fucose (Fuc), N-acetyl-D-galactose amine (GalNAc), N-acetyl-D-glucose amine (GlcNAc), N-acetyl-D-neuraminic acid (NeuAc), D-arabinose (Ara) and D-xylose (Xyl) (the abbreviations in brackets are according to IUPAC-IUB's abridged terminology for monosaccharides, J. Biol. Chem., Vol. 257, pp. 3347–3354 (1982)). The number of combination possibilities will, however, be almost infinitely great because both the anomeric configuration ($\alpha$ or $\beta$) and the position of the O-glycosidic bond can be varied. As a result, considerable difficulties are encountered in the synthesis of oligosaccharides by conventional organic chemical synthesis. The organic chemical techniques employed require an extensive protective group chemistry with many stages of synthesis and, consequently, often low total yields. In view hereof, industrial production by this technique usually is disadvantageous.

Enzymes are nature's own catalysts with many attractive characteristics, such as high regio- and stereoselectivity as well as high catalytic efficiency under mild conditions. Today, great hopes are therefore placed in being able to utilise enzymes for large-scale selective synthesis of oligosaccharides with fewer stages of synthesis and, consequently, higher total yields than by organic chemical methodology.

Literature discloses a number of enzyme-catalysed oligosaccharide syntheses (K. Nisizawa et al, in "The Carbohydrates, Chemistry and Biochemistry", 2nd Ed., Vol. IIA, pp. 242–290, Academic Press, N.Y. (1970)). Both hydrolases (glycosidases, EC number 3.2) and transferases (EC number 2.4) have been used, and of these hydrolases in particular have been used for oligosaccharide synthesis. To bring about a glycosidic synthesis with this type of enzyme, two procedures were utilised: reverse hydrolysis (condensation or equilibrium technique) and transglycosidation (kinetic technique).

Reverse hydrolysis: $\text{DOH} + \text{HOA} \underset{\longleftarrow}{\overset{\text{EH}}{\longrightarrow}} \text{DOA} + \text{H}_2\text{O}$ (1)

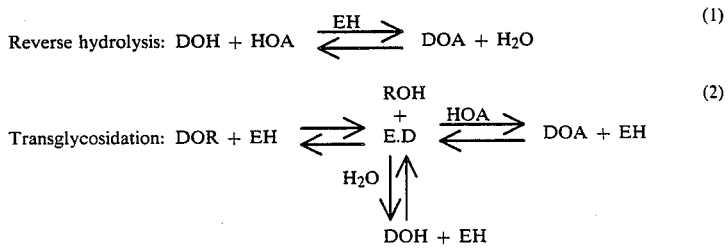

Transglycosidation (2)

(DOH is donor saccharide, DOR is donor saccharide with $\alpha$- or $\beta$-glycosidically bonded aglycon (=R), HOA is acceptor saccharide, and EH is enzyme.)

Reverse hydrolysis can give high yields if the product is insoluble, or if the reaction can be carried out with organic solvents in order to lower the water concentration. For transglycosidation, the high enzymatic activity against donor substances, such as phenyl or nitrophenyl glycosides (R=phenyl, nitrophenyl in equation 2) has been utilised in order to obtain a high product yield.

Even though these techniques have proved to be entirely useful in many situations, the difficulty has been to control the reactions such that the donor substance is bonded O-glycosidically to the desired position on the acceptor substance. Usually, 1-6 bonds (or bonds to primary hydroxyl groups on the acceptor saccharides) have been formed, while 1-2, 1-3 and 1-4 bonds which occur most frequently in glycoconjugates, have not been formed, or formed to a less extent. Furthermore, prior art techniques frequently result in the formation of not readily purified isomeric product mixtures because the reducing end is not glycosidated and therefore is present in the product solution as both the $\alpha$-anomer and the $\beta$-anomer. Moreover, prior art techniques have required further chemical modification of the products before they could be coupled to proteins, lipids etc.

One of the objects of this invention is to eliminate or reduce the disadvantages of prior art enzymatic techniques. In particular, it aims at providing facilities for controlling the regioselectivity in enzymatic carbohydrate synthesis so that the desired bond between donor and acceptor substances is formed to a higher degree than without such control. Other specific objects of the invention are to facilitate purification of the products and to facilitate direct synthesis of interesting glycosides of oligosaccharides.

The present invention thus relates to a method of controlling the regioselectivity of the glycosidic bond formed between glycosyl donor and glycosyl acceptor in the enzymatic production of an oligosaccharide compound which either consists of or is a fragment or an analog of the carbohydrate part in a glycoconjugate, by reverse hydrolysis or transglycosidation. The method is characterised in that a donor substance which is a monosaccharide or oligosaccharide or a glycoside of a monosaccharide or oligosaccharide, is caused to react with an acceptor substance which is an O-, N-, C- or S-glycoside consisting of a monosaccharide, oligosaccharide or a saccharide analog and at least one aglycon which is O-, N-, C- or S-glycosidically bonded in 1-position, in the presence of a glycosidase, the $\alpha$- or $\beta$-configuration being selected for the glycoside bond between the glycosyl group and the aglycon in the acceptor substance, and that the oligosaccharide compound is separated from the reaction mixture.

The acceptor substance utilised for the method according to the present invention is a glycoside of a mono- or oligosaccharide or an analog thereof having the formula HOAR$_2$ wherein R$_2$ is a glycosidically bonded inorganic or organic substance (R$_2$ is an aglycon, i.e. not a carbohydrate). The product in the method according to the invention is designated DOAR$_2$ symbolising compounds of the type D($\alpha$1-X)A($\alpha$)R$_2$, D($\alpha$1-X)A($\beta$)R$_2$, D($\beta$1-X)A($\alpha$)R$_2$ and D($\beta$1-X)A($\beta$)R$_2$ (D symbolises mono- or oligosaccharide; A symbolises mono- or oligosaccharide or an analog thereof; X represents 2, 3, 4 or 6; $\alpha$ and $\beta$, respectively, represent the configuration of the O-glycosidic bond between D and A, and of the O-, N-, S- or C-glycosidic bond between A and R$_2$). Examples of substances of this type are Gal($\alpha$1-3)Gal($\alpha$)-OMe, Gal($\alpha$1-3)Gal($\beta$)-OMe, GlcNAc($\beta$1-6)Man($\alpha$)-OMe and Man-($\alpha$1-2)Man($\alpha$)-OMe (abbreviations according to IUPAC-IUB's recommendations for abridged oligosaccharide terminology; J. Biol. Chem., Vol. 257, pp. 3347-3354 (1982)).

The reaction sequences for, respectively, reverse hydrolysis and transglycosidation will then be the following for the method according to the invention:

Reverse hydrolysis: DOH + HOAR$_2$ $\xrightleftharpoons{EH}$ DOAR$_2$ + H$_2$O     (3)

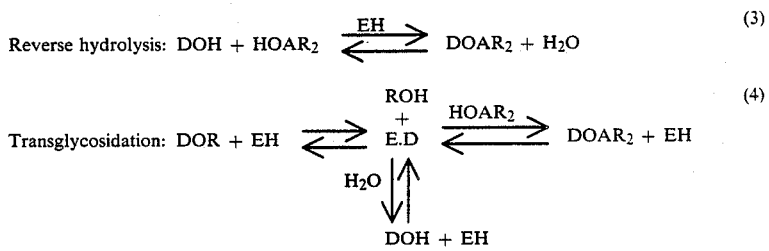

(4)

The difference between the earlier reactions and the reactions according to the invention is that the acceptor substances used in reactions (1) and (2) were substances of the type HOA, i.e. substances which are not derivatised in 1-position, whereas the present invention uses acceptor substances which are derivatised in 1-position, i.e. of the type HOAR$_2$. The earlier product thus was of the type DOA, whereas the product in the method according to the invention will be of the type DOAR$_2$.

The donor substance, on the other hand, is selected with regard to the oligosaccharide which is to be synthesised, and whether the synthesis is to be carried out with reverse hydrolysis or with transglycosidation. Consequently, the donor may be a mono- or oligosaccharide which is non-derivatised or is derivatised at its reducing end with a glycosidically bonded organic substance. The organic substance may be aliphatic, aromatic, heterocyclic etc., and may be glycosidically bonded to the 1-position of D (DOR, cf. equation 2) or (4) in $\alpha$- or $\beta$-configuration. Examples of derivatised donor substances that may be used according to the invention are methyl, CH$_3$(CH$_2$)$_n$ (n>0), phenyl, p-nitrophenyl, o-nitrophenyl, 4-methylumbelliferyl glycosides. A large number of donor substances of this type are commercially available. If not, they are readily synthesised by organic or enzymatic synthesis and therefore do not restrict the use of the invention. Examples of useful oligosaccharides are lactose, raffinose, chitobiose and dimannoside. Different glycosidases with activity against different types of alkyl or aryl glycosides are thoroughly described in literature, and the expert therefore has no difficulty in selecting a suitable group R satisfying the requirements in each individual case.

The enzyme is selected with due regard to the requirements in each particular case, primarily with regard to which oligosaccharide is to be synthesised. For example, an α-glycosidase is required in the synthesis of an α-glycosidic bond, while a β-glycosidase is required in the synthesis of a β-glycosidic bond. Preferred enzymes are endoglycosidases and exoglycosidases from group EC 3.2. Examples of enzymes that may be used according to the invention are the following α- and β-glycosidases: D-mannosidases, D-galactosidases, L-fucosidases, neuraminidases, N-acetyl-D-glucosaminidases, N-acetyl-D-galactosaminidases, xylosidases, hexosaminidases and the other glycosidases of group EC 3.2 (Enzyme Nomenclature, Academic Press, pp. 1–606, N.Y. (1979); Enzymes, 3rd Ed., Dixon et al, Longman (1979)).

The degree of purity of the enzyme employed is not critical. The enzyme may be used in situ or after complete or partial isolation from its natural biological environment. Intact or freeze-dried cells as well as more or less purified enzymes may be used. The enzyme may be present in crystalline form or be enclosed within micelles. A very large number of glycosidases from different types of cells are commercially available. Besides, the biochemical literature is very rich in detailed information about the purification and isolation of interesting glycosidases.

The enzymes may be used in soluble form or may be immobilised by precipitation, adsorption, enclosure, chelation or covalent bonding to a solid phase, such as a polymeric substance, or a derivative thereof which is insoluble in protic or aprotic solvents (Methods in Enzymology, Vol. 44, Academic Press, (1976)). The form selected is not critical to the invention. If the enzyme is used in soluble form, it may first have been chemically modified in some suitable manner, for example in order to increase the stability against elevated temperatures or organic cosolvents. Enzyme immobilised to an insoluble polymer comprising, for example, agarose, cellulose, hydroxyethyl acrylate, glass, silica, polyacrylamide, polyacrylate-based plastics, etc., is readily separated from the product mixture, and the enzyme may thus be reused. An additional advantage is that in many cases a certain stabilisation against elevated temperatures and organic cosolvents is obtained.

The selection of the acceptor substance is decided by the oligosaccharide one wishes to synthesise. The same types of monosaccharides as are included in the donor substance may be included in the acceptor, preferably one or more of the following: Glc, Gal, Man, Fuc, Xyl, Ara, GlcNAc, GalNAc and NeuAc (abbreviations according to IUPAC-IUB's recommendations, see above). The acceptor substance shall be derivatised by at least one aglycon which is O-, N-, C- or S-glycosidically bonded in 1-position.

According to the invention, the acceptor substance may also consist of saccharides derivatised in one or more positions besides the 1-position. Such derivatisation may imply, for example, that one or more hydroxyl groups have been replaced by hydrogen or an organic group. One example of such an acceptor substance is p-nitrophenyl-2-deoxy-α-D-galactopyranoside. Another important type of saccharide derivatives are substances in which the ring oxygen (i.e. C-5 oxygen in hexoses) has been replaced by nitrogen, sulphur etc. One example of such a derivative is the glucose analog moranoline in which C-5 oxygen has been replaced by nitrogen. Oligosaccharide analogs that are efficient inhibitors against enzymes or carbohydrate-bonding proteins may, in this manner, be synthesised in accordance with the present invention.

The aglycon $R_2$ in $HOAR_2$ may be of varying type, and the selection is decided by what is required and desired in each particular case. $R_2$ may be an inorganic substance, but above all $R_2$ may be an organic substance of varying type (aliphatic, aromatic, heterocyclic, heteroaromatic, or variations thereof). $R_2$ may be O-, N-, S- or C-glycosidically bonded to the acceptor saccharide. As examples of suitable organic aglycons, mention may be made of $CH_3(CH_2)_n$ groups, such as methyl wherein $n=0$ or ethyl wherein $n=1$ or other alkyl groups wherein $n \geqq 1$, e.g. octyl wherein $n=7$ or dodecyl wherein $n=11$; phenyl, p-nitrophenyl and o-nitrophenyl groups; 2-bromoethyl, trimethylsilyl ethyl or $CH_2=C(CH_3)-C(O)-O-CH_2CH_2$ groups. The aglycon may also be an amino, nitrile or amide group, or a fluorogenic substance, or it may contain a phosphate, sulphate or carboxyl group, or derivatives thereof.

Products obtained with alkyl glycosides (such as methyl, octyl, dodecyl glycosides) as acceptor substances may be used as inhibitors for agglutination tests or for affinity chromatography. They may also be utilised for inhibition-based therapy, or for drug targeting, as structural units for continued enzymatic or organic synthesis, etc. Nitrophenyl glycosides may be simply reduced with, for example, Pd/C to aminophenyl glycosides which, directly or after chemical modification, can be coupled covalently to different polymers (dextran, polyethylene glycol, agarose, cellulose, silica etc.) as well as to peptides, proteins, enzymes, lipids, or analogs thereof, etc. (Methods in Enzymology, Academic Press, Vols. 34, 44, 50 and 104). Moreover, the amino group is readily convertible into several other reactive groups, such as isothiocyanate, diazo, N-bromoacetate, etc. Other groups which, directly or after chemical modification, may be used as so-called spacer arm in (Methods in Enzymology, Vol. 34, Academic Press) the manner described above for the amino phenyl group, and which are useful as aglycon ($R_2$ group) according to the invention are, for example, 2-bromoethyl, 2-(2-carbomethoxyethylthio)ethyl, 2-aminoethyl and 6-aminohexyl groups or derivatives thereof. Also glycosides with polymerisable aglycon, such as 2-hydroxyethyl methacrylate, may be used as acceptor substances. As an example of N-glycosidically bonded aglycon mention may be made of 6-amino caproic acid amide ($-NHCO(CH_2)NH_2$).

Another type of glycosides are trimethylsilyl ethyl glycosides which are interesting because they permit replacing the trimethylsilyl group by an acetyl group while retaining the anomeric configuration (K. Jansson et al, Tetrahedron Lett., 27 (1986), 753–756). A single enzymatic step can thus make it possible to synthesise a large number of glycosides of the same oligosaccharide sequence. Allyl and benzyl glycosides are readily converted to free sugar. The allyl group is removed with, for example, KotBu/DMSO, 70° C., followed by $HgCl_2 \cdot HgO$/acetone. The benzyl group is readily removed with Pd/C. Allyl glycosides may be converted into the corresponding 2,3-epoxypropyl glycosides (E. Falent-Kwast et al, Carbohydrate Res., 145 (1986), pp. 332–340). Oligosaccharide sequences with a free reducing end may thus be synthesised.

Other aglycons of special interest are amino acids (serine, threonine, hydroxy proline, hydroxy lysine, asparagine, etc.), peptides, lipids and derivatives or analogs to substances within these three groups. The amino acid and peptide glycosides may be protected on their amino and/or carboxyl functions by conventional groups utilised in peptide synthesis (FMOC, CBZ, BOC, etc.). According to the invention, fragments or analogs of glycoconjugates can be synthesised with these aglycons.

As mentioned above, it is an important advantage of the synthesis method according to the invention that the synthesis can be controlled such that the desired position of the acceptor substance will be glycosidically substituted. As a result, the desired oligosaccharide isomer is formed in a higher degree than with prior art methods. A further advantage is that the same enzyme can catalyse the synthesis of different isomers in different degrees, depending on the selection of aglycon and the configuration of its glycosidic bond to the saccharide portion in the acceptor substance.

Purification of the products also is greatly facilitated in most cases since, with the method according to the invention, one is spared the problem of isomerisation on the anomeric carbon at the reducing end of the product.

Still another advantage is that interesting fine chemicals can be synthesised with the method according to the invention. Substances that may be used, directly or after chemical modification, for e.g. polymerisation, for immobilisation to solid carriers, or for bonding to enzymes or proteins, are obtainable. The synthesis of glycopeptides and glycolipids and analogs thereof may also be greatly facilitated by the method according to the invention since amino acid, peptide or lipid derivatives may be used as aglycons.

The synthesis method according to the invention can be carried out under highly diverse conditions as regards, for example, temperature, pH, buffer and concentration of reactants. Various cosolvents (N,N-dimethyl formamide, acetonitrile, dimethyl sulfoxide, dioxane, pyridine, methanol, ethanol, ethylene glycol, etc.) may be used and in varying concentrations together with water. In addition, the reactions can be carried out in two-phase system, water-organic solvent (cyclohexane, chloroform, methylene chloride, etc.). The enzyme may then be enclosed in inverse micelles (P. Luisi, Angew. Chem., Vol. 97, pp. 449–60, (1985)). The reactions may also be carried out in a pure organic solvent with precipitated enzyme (Kazandjian et al, J. Amer. Chem. Soc., Vol. 107, (1985)). The reaction conditions are not critical, but are selected primarily on the basis of the properties of the reactants included in the synthesis concerned, and also for practical reasons. For example, it may be mentioned that, with enzymes, it is frequently suitable to work at room temperature, and in the case of an aqueous medium with a pH in the range 4–11. It has been found that a higher product yield is frequently obtained by using a pH which is somewhat higher than the optimal pH of the enzyme. Thus, use was made of pH 6.5–7.5 for $\alpha$-galactosidase from coffee bean, and for $\alpha$-mannosidase from jack bean, while a somewhat higher pH is favourable for $\beta$-galactosidase from E. coli. Suitable buffer salts are, for example, sodium acetate, potassium acetate, potassium phosphate, or sodium phosphate.

Organic cosolvents may be used in order to minimise hydrolysis reactions. For the same reason, use may be made of two-phase systems. It has been found, however, that in some cases the yield will be much higher if water is used as the only solvent, and this applies to the synthesis of, for example, Gal($\alpha$1-3)Gal($\alpha$)-OMe and Gal($\alpha$1-3)Gal($\alpha$)-OC$_6$H$_4$—NO$_2$—P with $\alpha$-galactosidase from coffee bean.

The temperature may also be varied in order to influence product yield and enzyme stability. The temperature most frequently used lies in the range 5°–55° C., but higher temperatures may be used with thermostable glycosidases and with enzymes stabilised against thermal denaturation with, for example, high substrate concentrations (E. Johansson et al, Biotechnol. Lett., 8 (1986) pp. 421–442). One of the advantages of a high temperature is that use may be made of high substrate concentrations, whereby the water activity is reduced and a higher product yield is obtained. A further advantage is an increase in enzyme activity, which brings shorter reaction times at higher temperatures, and this again brings the advantage that glycosides which are hydrolysed relatively slowly at room temperature, such as methyl or ethyl glycosides, may be advantageously used as glycosyl donors at higher temperatures (50°–60° C.). The upper temperature limit is determined by the thermostability of the enzyme in the reaction medium. For some transglycosidations, a lower temperature was found to give a higher yield of product glycoside. Thus, a maximum yield was obtained at 20° C. of Gal($\alpha$1-3)Gal($\alpha$)-OMe with 0.15M initial concentration of donor and 0.45M concentration of acceptor with $\alpha$-galactosidase from coffee bean when the reaction was carried out at 20°, 40° and 50° C., respectively.

Normally, use is made of saturated solutions of donor and acceptor substances in order to achieve maximum yields of product glycosides. This means 0.05–0.2 molar solutions of p-nitrophenyl glycosides, and 0.3–0.6 molar solutions of methyl glycosides at room temperature and with water as solvent. Cosolvents, such as methanol, N,N-dimethyl formamide, may be used for increasing the solubility of glycosides with hydrophobic aglycon, for example p-nitrophenyl glycosides. The reaction can be monitored by means of TLC, HPLC or by spectrophotometrical determination of released aglycon (for example p-nitrophenol, 400 nm). When maximum yield of the product glycoside has been achieved, the reaction is interrupted by denaturation of the enzyme by changing the pH, increasing the temperature and/or adding organic cosolvent (such as ethanol). Heating to 80°–85° C. for 3–5 min, followed by an addition of ethanol to a concentration of about 80%, usually is sufficient.

Different techniques may be employed to purify the product. Useful is column chromatography with, for example, methylene chloride:methanol:water (e.g. 6:4:1 v/v/v) as eluant, and silica as solid phase, whereupon the partially purified product glycoside after drying at low pressure is acetylated with acetic anhydride and pyridine (e.g. 1:1 v/v). A further column chromatographical step (silica, eluant, for example ethyl acetate:isooctane) usually gives a pure acetylated product. Deacetylation in dry MeOH with a catalytic amount of sodium methoxide frequently gives crystalline product glycoside. The purification of products with markedly hydrophobic aglycons (for example Gal($\alpha$1-3)Gal-($\alpha$)OC$_6$H$_4$NO$_2$-p) may frequently be carried out in one step with preparative HPLC equipment and C$_{18}$ silica.

The synthesis method according to the invention is generally applicable to the synthesis of oligosaccharide sequences included in glycoproteins or glycolipids (Biology of Carbohydrates, Vol. 2 (1984), V. Ginsburg and P. W. Robbins, eds. Wiley & Sons, N.Y.; The Glycoconjugates, Vol. I-V, Academic Press, N.Y.; S. Hakomori, Ann. Rev. Biochem., Vol. 50, pp. 733–64 (1981)).

Of special interest are the minutest fragments of these structures, which are sufficient to transfer biological information. As examples of important such structures, mention may be made of the blood group determinants, specific receptors for microorganisms (Gal(α1-3)Galα-, E. coli K88; ClcNac(β1-3)Galβ-, S. pneumoniae; Gal-(α)1-4)Galβ-, p-fimbriated E. coli; etc.), the differentiation antigens i, I, CO 514, 38.13, etc. (see Tables 1 and 2 in the Review Article by T. Feizi, Nature, Vol. 314, pp. 53–57 (1985)).

For example, oligosaccharide sequences included in the following N-bonded oligosaccharides may be produced which are representative of three classes of "mature" asparagine-bonded oligosaccharides, viz. (a) higher mannose type, (b) complex type, (c) hybrid type (see Biology of Carbohydrates, Vol. 2, (1984), V. Ginsburg and P. W. Robbins, eds. Wiley & Sons, N.Y.):

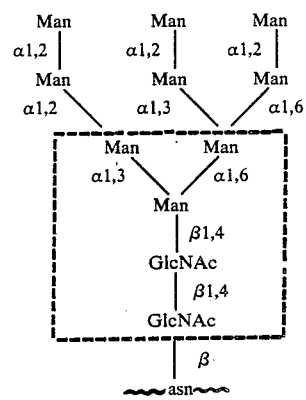

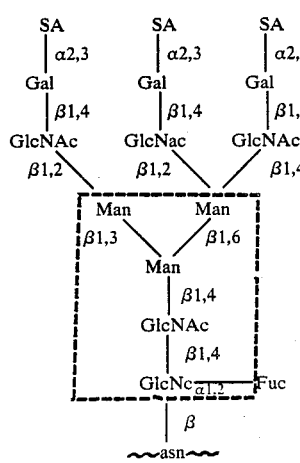

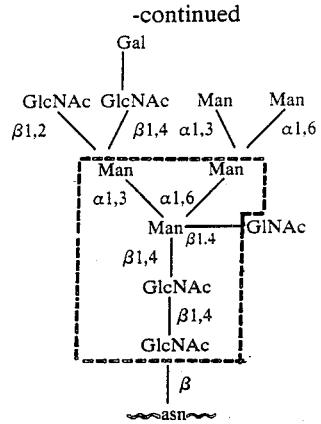

The oligsaccharide sequences included in the following O-bonded oligosaccharide structures can be produced (see Biology of Carbohydrates, Vol. 2 (1984), Wiley, N.Y.):

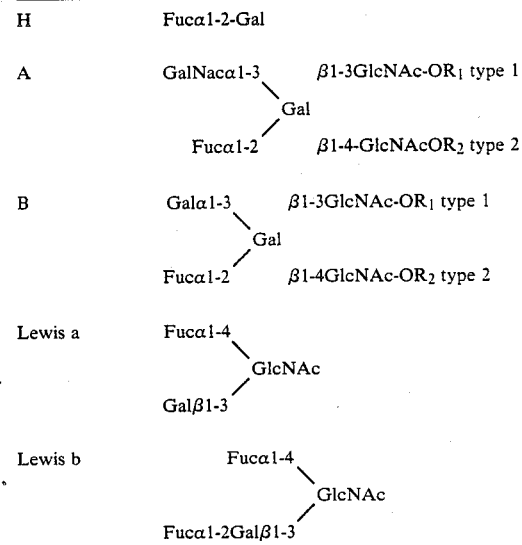

| II. Other Sugars | |
|---|---|
| Fucose | 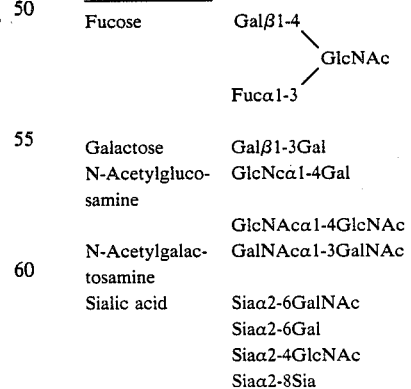 |
| Galactose | Galβ1-3Gal |
| N-Acetylglucosamine | GlcNcα1-4Gal |
| | GlcNAcα1-4GlcNAc |
| N-Acetylgalactosamine | GalNAcα1-3GalNAc |
| Sialic acid | Siaα2-6GalNAc |
| | Siaα2-6Gal |
| | Siaα2-4GlcNAc |
| | Siaα2-8Sia | as can the following specific structures of branches of O-bonded glycoproteins:

| Branch | Structures Attached | | |
|---|---|---|---|
| | Lacto N-biose linkage | (Lewis) or Fucα-ABH | Fucα1-4GlcNAc 3GlcNAc |
| I. GlcNAcβ1-6GalNAc | Type 1 | B,H | Yes |
| II. GlcNAcβ1-3GalNAc | Type 2 (only) | None | None |
| III. Galβ1-3GalNAc | — | A,B,H | — |
| IV. GlcNAcβ1-6Gal | Type 2 (only) | H | Yes |
| V. GlcNAcβ1-3Gal | Type 1 Type 2 | A,B,H A,H | Yes Yes |

Further structures or fragments thereof that can be prepared according to the invention are the following (see S. Hakomori, Ann. Rev. Biochem., Vol. 5, p. 739 (1981):

Ganglio-series $^{a}$Galβ1⟶3GalNAcβ1⟶4Gal$^{b}$β1⟶4Glcβ1⟶1Cer

GalNAcβ1⟶4Gal$^{b}$β1⟶3GalNAcβ1⟶4Gal$^{b}$β1⟶4Glcβ1⟶1Cer

Globo-series $^{c}$GalNAcβ1⟶3Galα1⟶4Galβ1⟶4Glcβ1⟶1Cer

GalNAcβ1⟶3Galα1⟶3Galβ1⟶4Glcβ1⟶1Cer

Lacto-series $^{d}$Galβ1⟶4GlcNAcβ1⟶3Galβ1⟶4Glcβ1⟶1Cer

Galβ1⟶3GlcNAcβ1⟶3Galβ1⟶4Glcβ1⟶1Cer $^{d}$Galβ1⟶4GlcNAcβ1⟶3Galβ1⟶4GlcNAcβ1⟶3Galβ1⟶4Glcβ1⟶1Cer $^{d}$Galβ1⟶4GlcNAcβ1
　　　　　　　　　↘6
　　　　　　　　　　Galβ1⟶4GlcNAcβ1⟶3Galβ1⟶4Glcβ1⟶1Cer
　　　　　　　　　↗3
$^{d}$Galβ1⟶4GlcNAcβ1

Muco-series $^{e}$Galβ1⟶3Galβ1⟶4Glcβ1⟶1Cer $^{e}$Galβ1⟶3Galβ1⟶3Gal$^{f}$β1⟶4Glcβ1⟶1Cer Gala-series Galα1⟶4Galβ1⟶1Cer The Table below shows some suggested receptor structures for microorganisms and toxins that may, wholly or partly, be produced according to the invention:

| Strain (organism)/adhesin Site of infection | Suggested specificity | Ref. |
|---|---|---|
| *E. coli* | | |
| type 1 fimbriae Human urinary tract | Man | (a) |
| F-fimbriae Human urinary tract | Galα1-4Galβ-O | (b) |
| X-fimbriae | NeuAcα2-Gal, GlcNAcβ1-O— | (c,d) |
| K88 pig, small intestine | Galα1-3Gal-α1-O | (e) |
| K99, calf, small intestine | GalNac, NeuAc | (f) |
| Shigella-toxin | Galα1-4Gal-terminal position | (g) |
| *S. saprophyticus* Human urinary tract | Galβ1-4GlcNAcβ-O | (h) |

| Strain (organism)/adhesin Site of infection | Suggested specificity | Ref. |
|---|---|---|
| | GlcNAcβ1-4GlcNAc-OH | |
| *S. pneumococcus* Human respiratory tract | GlcNAcβ1-3Galβ-O | (i) |
| *M. pneumoniae* Human respiratory tract | Lactosamine 1 | (j) |

NeuAcα2-3Lactosamine 1

| Influenza virus Human respiratory tract | NeuAc-Gal | (k) |
|---|---|---|

| Strain (organism)/adhesin Site of infection | Suggested specificity | Ref. |
|---|---|---|
| Vibrio cholera and piliated gonococcus Intestine/human urinary tract. | Galβ1-3GalNAcβ1-4Galβ1-4Glc (GM)₁ | (l) |

Also of great interest is the large number of different oligosaccharide sequences in glycoconjugates which occur in different human tumours and which act as tumour-associated antigens (see int.al. Feizi, Nature, 314 (1985)) where the following structures are described:

| Structure | Cell Association |
|---|---|
| Galβ1⟶4GlcNAc<br>NeuAc ↑1,3<br>Fucα | Colorectal cancer, human |
| Galβ1⟶4GlcNAc<br>↑1,2    ↑1,3<br>Fucα   Fucα | Colonic adenocarcinoma, human<br>Lung adenocarcinoma, human<br>Gastric cancer, human<br>Embryonal carcinoma cells, human and mouse |
| Galα1⟶3Galβ1⟶4GlcNAc<br>↑1,2<br>Fucα | Pancreatic cancer |
| Galβ1⟶3GlcNAcβ1⟶3Galβ1⟶<br>⟶4Glc/GlcNAc | Embryonal carcinoma cells, human; gastric mucosa, non-secretors; gastric adenocarcinoma secretors |
| Galβ1⟶3GlcNAc<br>↑1,2    ↑1,4<br>Fucα   Fucα | Adenocarcinomas, human |
| Galβ1⟶3GlcNaC<br>↑2,3    ↑1,4<br>NeuAcα Fucα | Colon cancer, human normal pancreatic ducts |
| Ganglio-series<br>GalNAcβ1⟶4Galβ1⟶4Glc-Cer<br>↑2,3<br>NeuAcα | Melanoma and fetal brain, human |

(a) N. Firon, I. Ofek and W. Sharon, Infect. Immun., 43, 1984, p. 1088; E. H. Beachey (ed) Bact. Adherence, Receptors and Recognition, Vol. 8, Chapman and Hail, N.Y., 1980.
(b) H. Leffler and C. Svanborg-Ed'en, FEMS Microbiol. Letters 8, 1980, p. 127; G. Kallenius, R. Mollby, S. B. Svensson, J. Winberg, A. Lundblad, S. Svensson, and B. Cedergren, FEMS Microbiol. Letters 7, 1980, p. 297.
(c) I. Parkkinen, J. Finne, M. Achtman, V. Vaisanen, and T. K. Korhonen, Biochem. Biophys. Res. Commun. 111, 1983, p. 456.
(d) V. Vaisanen-Rhen, T. K. Korhonen, and J. Finne, FEBD Lett. 159, 1983, p. 233.
(e) M. J. Anderson, J. S. Whitehead, and Y. S. Kim, Infect. and Immun, 29, 1980, p. 897.
(f) M. Bertolini and W. Pigman, Carbohydr. Res., 14, 1978, p. 53.
(g) J. E. Brown, K.-A. Karlsson, A. Lindberg, N. Stromberg, and J. Thurin in M. A. Chester, D. Heinegard, A. Lundblad, and S. Svensson (eds), Proc. 7th Int. Symp. Glyco-conjugates, Lund, 1983, p. 678.
(h) A. Gunnarsson, P.-A. Mardh, A. Lundblad, S. Svensson, Infect. Immun., 45, 1984, p. 41.
(i) C. Svanborg-Eden, B. Andersson, L. Hagberg, H. Leffler, G. Magnusson, G. Moori, J. Dahmen, and T. Soderstrom, Ann. N.Y. Acad. Sci., 409, 1983, p 560.
(j) T. Feizi and R. A. Childs, Trends. Biochem. Sci., 10, 1985, p. 24.
(k) G. F. Springer and R. R. Desai, Ann. Clin. Lab. Sci., 1985, p. 294.
(l) J. Holmgren, Nature, 292, 1981, p. 431.

Oligosaccharide sequences containing monosaccharide analogs, such as fluoro-, phospho-, amino- or thioanalogs are of great interest to the study of glycoconjugate metabolism, and potentially to the chemotherapy of cancer (The Glycoconjugates, Vol. IV (1982) Academic Press). Some oligosaccharide analogs have been shown to have a higher association constant to lectins than the natural receptor. This is of considerable interest to the development of sensitive diagnostics and efficient therapeutics based on carbohydrate structures.

As has been mentioned before, a large number of aglycons may be used. By selecting for example allyl, benzyl or trimethylsilyl glycosides as acceptors, the free sugar may be readily obtained from the product glycoside in high yield. Enzymatic synthesis of free oligosaccharide structures which previously could not be synthesised with glycosidases may thus be carried out by means of the method according to the invention.

Simple glycosides (such as methyl glycosides) may be used for inhibition studies with antibodies (Slama et al, Biochemistry, (1980), 19(20), 4595–4600) and lectins (Sharon and Lis, Science (1972), 177, 949–959). Glycosides with chromophore or fluorescent aglycons (e.g. p-nitrophenyl, 4-methylumbelliferyl) may be used for enzyme analysis (D. E. Sykes et al, Carbohydrate Res., 116 (1983) 127–138). Glycosides suitable for covalent bonding to peptides, proteins, lipids, carriers for chromatography etc. may also be synthesised by the method according to the invention.

Some examples of how the invention may be used in actual practice are described in the following Examples which, however, are in no way intended to restrict the scope of the invention (abbreviations according to IUPAC-IUB's recommendations, J. Biol. Chem. Vol. 257, pp. 3347–3354 (1982)).

EXAMPLE 1

Synthesis of Gal($\alpha$1-3)Gal($\alpha$)-OMe
(methyl-3-O-$\alpha$-D-galactopyranosyl-$\alpha$-D-galactopyranoside)

A. 1.8 g p-nitrophenyl-$\alpha$-D-galactopyranoside (Gal($\alpha$)-OPhNO$_2$-p; and 18 g 1-O-methyl-$\alpha$-D-galactopyranoside (Gal($\alpha$)-OMe) were dissolved in 110 ml 0.05M aqueous solution of sodium phosphate (pH 6.5) and 40 ml N,N-dimethyl formamide. $\alpha$-galactosidase ($\alpha$-D-galactoside galactohydrolase; EC 3.2.1.22; 0.2 ml; 10 units, Boehringer) from coffee bean were added. After 7 days at room temperature, the reaction mixture was heated at 80° C. for 5 min, and the product was purified by column chromatography (silica, Kieselgel 60, 230–400 mesh, Merck, chloroform:MeOH:H$_2$O, 6:4:0.5 v/v) and was peracetylated with acetic anhydride and pyridine. After a further column chromatographical step (silica, isooctane:ethyl acetate, 1:1 v/v) and deacetylation in MeOH with catalytic amounts of sodium methoxide, pure crystalline Gal($\alpha$1-3)Gal($\alpha$)-OMe was obtained. The product was analysed with NMR, HPLC (>99% purity) and methylation analysis.

B. 0.31 g Gal($\alpha$)-OPhNO$_2$-p and 0.91 g Gal($\alpha$)-OMe were dissolved in 10 ml buffer (see Example 1A, above). $\alpha$-galactosidase (coffee bean, Boehringer, EC 3.2.1.22; 5 units) was added, and the reaction was allowed to continue at room temperature for 72 hours. The reaction mixture was heated to 80° C. for 5 min, and the products were isolated in accordance with Example 1A, above. The yield of Gal($\alpha$1-3)Gal($\alpha$)-OMe was 180 mg or 39% of Gal($\alpha$)-OPhNO$_2$-p added.

EXAMPLE 2

Synthesis of Gal($\alpha$1-3)Gal($\beta$)-OMe and Gal(h1-6)Gal($\beta$)-OMe 0.6 g Gal($\alpha$)-OPhNO$_2$-p and 4 g Gal($\beta$)-OMe were dissolved in 22 ml 0.05M aqueous solution of sodium phosphate (pH 6.5) and 9 ml N,N-dimethyl formamide. $\alpha$-galactosidase from coffee bean (EC 3.2.1.22; 0.2 ml; 10 units was added, and the reaction was allowed to continue at room temperature for 90 hours. The products were purified by column chromatography in accordance with Example 1. Acetylated products were analysed with 200 MHz NMR ($^1$H, $^{13}$C). The yield of Gal($\alpha$1-6)Gal($\beta$)-OMe was 125 mg, and of Gal($\alpha$1-3)Gal($\beta$)-OMe 65 mg or 16 and 8%, respectively, of the added amount of Gal($\alpha$)-OPhNO$_2$-p.

EXAMPLE 3

Synthesis of Gal($\alpha$1-2)Gal($\alpha$)-OPhNO$_2$-p and Gal($\alpha$1-3)Gal($\alpha$)-OPhNO$_2$-p A. 0.9 g Gal($\alpha$)-OPhNO$_2$-p was dissolved in 24 ml 0.05M aqueous solution of sodium phosphate (pH 6.5) and 8 ml N,N-dimethyl formamide. $\alpha$-galactosidase from coffee bean (EC 3.2.1.22; 0.2 ml; 10 units) was added, and the reaction was allowed to continue for 38 hours at room temperature. The products were separated by column chromatography (silica, Sephadex G10) and analysed with UV (305 nm), 200 MHz NMR ($^1$H, $^{13}$C) and by methylation analysis. The yield of Gal($\alpha$1-3)Gal($\alpha$)-OPhNO$_2$-p was 150 mg and of Gal($\alpha$1-2)Gal($\alpha$)-OPhNO$_2$-p 25 mg, i.e. 13 and 1.7%, respectively, of the added amount of Gal($\alpha$)-OPhNO$_2$-p.

B. 1.35 g Gal($\alpha$)-OPhNO$_2$-p were dissolved in 10 ml buffer (see Example 3A, above), and 5 units $\alpha$-galactosidase from coffee bean (see Example 3A, above) were added. The reaction was allowed to continue for 76 hours at 50° C. The reaction was interrupted by heating the mixture at 80° C. for 5 min. The products were isolated by column chromatography (Sephadex G10, Pharmacia, and silica, Merck, Kieselgel 60, 23–400 mesh, ethyl acetate:isopropanol:water 6:2:1, v/v/v), according to Example 3A, above. The yield of Gal($\alpha$1-3)Gal($\alpha$)-OPhNO$_2$ and Gal($\alpha$1-2)Gal($\alpha$)-OPhNO$_2$-p was 23% (236 mg) and 3.5% (36 mg), respectively.

C. This test was carried out in accordance with Example 3A, using $\alpha$-galactosidase from coffee bean, which had been immobilised to tresyl chloride-activated agarose (Pharmacia) (K. Nilsson et al, Biochem. Biophys. Res. Comm., 102 (1981) 449–457). 0.5 g, 11 units $\alpha$-galactosidase-agarose was added to 1.5 g Gal($\alpha$)-OPhNO$_2$-p dissolved in 23 ml buffer and 10 ml DMF. The reaction was allowed to continue under gentle agitation for 12 days at room temperature. Termination and isolation of the products as described above gave 160 mg Gal($\alpha$1-3)Gal($\alpha$)-OPhNO$_2$-p, or 14% of the theoretical yield. The immobilised $\alpha$-galactosidase could be used for repeated synthesis with but a few per cent reduced catalytic activity.

EXAMPLE 4

Synthesis of Gal($\alpha$1-2)Gal($\alpha$)-OPhNO$_2$-o 2 g Gal($\alpha$)-OPhNO$_2$-o were dissolved in 30 ml buffer (see Example 1A) and 14 ml DMF. $\alpha$-galactosidase (see Example 1A, 20 units) was added, and the reaction was allowed to continue for 53 hours at room temperature. The reaction was terminated, and the products were isolated and analysed as in Example 1A. The yield of pure crystalline Gal($\alpha$1-2)Gal($\alpha$)-OPhNO$_2$-o was 60 mg, or 4% of the theoretical yield.

EXAMPLE 5

Synthesis of Gal($\alpha$1-3)Gal($\alpha$)-OPhNO$_2$-p with $\alpha$-galactosidase from *Aspergillus niger*

The synthesis was carried out in accordance with Example 3, but with $\alpha$-galactosidase (EC 3.2.1.22) from *Aspergillus niger*. In this instance, 40 mg Gal($\alpha$1-3)Gal($\alpha$)-OPhNO$_2$-p and 4 mg of an isomeric product (presumably the ($\alpha$1-2) isomer) and traces (about 1 mg) of a further isomeric product were obtained. These isomers were separated in the Sephadex G10 step according to Example 3A.

EXAMPLE 6

Synthesis of Man(α1-2)Man(α)-OPhNO2p (p-nitrophenyl-2-O-α-D-mannopyranosyl-α-D-mannopyranoside)

0.63 g Man(α)-OPhNO2-p was dissolved in 33 ml 0.05M sodium phosphate (pH 6.5) with 10 μM ZnCl2. 10 ml N,N-dimethyl formamide were added. α-mannosidase (α-D-mannoside mannohydrolase; EC 3.2.1.24; 0.3 ml; 10 units Boehringer-Mannheim) from Canavalia ensiformis were added, and the reaction was allowed to continue for 6 hours at room temperature and 36 hours in a cooling chamber (4° C.). The product was isolated by column chromatography (silica gel) and analysed with NMR and methylation analysis. The yield of Man(α1-2)Man(α)-OPhNO2-p was 36 mg. The product had a purity of more than 95% according to NMR, and the remaining isomers were formed in a negligible extent.

EXAMPLE 7A

Synthesis of Man(α1-2)Man(α)-OMe (methyl-2-O-α-D-mannopyranosyl-α-D-mannopyranoside) and of Man(α1-6)Man(α)-OMe (methyl-6-O-α-D-mannopyranosyl-α-D-mannopyranoside)

0.6 g p-nitrophenyl-α-D-mannopyranoside (Man(α)-OPhNO2-p) and 6 g 1-O-methyl-α-D-mannopyranoside (Man(α)-OMe) were dissolved in 38 ml 0.05M aqueous solution of sodium phosphate (pH 6.5) with 10 μM ZnCl2. N,N-dimethyl formamide was added. α-mannosidase (EC 3.2.1.24; 0.3 ml; 15 units) from Canavalia ensiformis was added, and the reaction was allowed to continue at room temperature for 14 hours. The products were purified on silica column in analogy with the syntheses of Examples 1 and 2. The products were analysed with NMR, methylation analysis and HPLC. 180 mg Man(α1-2)Man(α)-OMe and 28 mg Man(α1-6)Man(α)-OMe were obtained, i.e. 20 and 3%, respectively, of the added amount of Man(α)-OPhNO2p.

EXAMPLE 7B

Synthesis of Man(α1-2)Man(α)-OMe and Man(α1-6)Man(α)-OMe 20 g Man(α)-OMe were dissolved in 45 ml buffer (see Example 7A) and 5 ml MeOH. α-mannosidase (see Example 7A, 50 units) was added, and the reaction was allowed to continue for 3 days at 55° C. The reaction was terminated, and the products were isolated in accordance with Example 7A.

EXAMPLE 8

Synthesis of Man(α1-2)Man(α)-OEtBr (2-bromoethyl-2-O-α-mannopyranosyl-α-D-mannopyranoside)

0.9 g Man(α)-OPhNO2-p and 2.7 g 2-bromoethyl-α-D-mannopyranoside (Man(α)-OEtBR) were dissolved in 20 ml 0.05M aqueous solution of sodium phosphate (pH 6.5). 7 ml N,N-dimethyl formamide were added. α-mannosidase (EC 3.2.1.24; 0.3 ml; 15 units) from Canavalia ensiformis was added, and the reaction was allowed to continue at room temperature for 72 hours. The product was purified in accordance with Example 7A. The product was analysed with NMR (200 MHz; 1H, 13C). 200 mg Man(α1-2)Man(α)-OEtBr were obtained and about 30 mg of an unidentified isomeric product (presumably the (α1-6) isomer).

EXAMPLE 9

Synthesis of Man(α1-2)Man(α1-2)Man(α)-OMe

This substance was formed as a by-product in large-scale synthesis of Man(α1-2)Man(α)-OMe and Man(α1-6)Man(α)-OMe from 20 g Man(α)-OPhNO2-p and 45 g Man(α)-OMe with 1 ml (50 units) of α-mannosidase from Canavalia ensiformis (EC 3.2.1.24), and otherwise under the conditions according to Example 7A. The product was separated from the disaccharide fractions by column chromatography (Sephadex G10, silica). The acetylated product was separated from isomeric products (about 35% of the total amount) by column chromatography (silica). 250 mg acetylated Man(α1-2)-Man(α1-2)Man(α)-OMe were obtained. The product was analysed with NMR (200 MHz; 1H, 13C) and by methylation analysis.

EXAMPLE 10

Synthesis of Gal(β1-3)Gal(β)-OMe (methyl-3-O-β-D-galactopyranosyl-β-D-galactopyranoside)

A. 2.7 g o-nitrophenyl-β-D-galactopyranoside (Gal(β)-OPhNO2-o) and 5 g Gal(β)-OMe were dissolved in 35 ml 0.05M aqueous solution of sodium phosphate (pH 6.8) with 1 mM MgCl2 and 10 mM mercaptoethanol. 15 ml N,N-dimethyl formamide were added. β-galactosidase (β-D-galactosidase galactohydrolase; EC 3.2.1.23; 100 units, Sigma Laboratories) from Escherichia coli was added, and the reaction was allowed to continue for 24 hours at room temperature. The products were separated by column chromatography (silica and Sephadex G10). After acetylation and chromatography on silica column, 1.3 g acetylated Gal(β1-3)Gal(β)-OMe and 160 mg Gal(β1-6)Gal(β)-OME (acetylated) were obtained. Analysis with 200 MHz NMR (1H, 13C).

B. This test was analogous to Example 10A, but use was made of 9.0 g Gal(β)-OPhNO2-o, 15 g Gal(β)-OMe and β-galactosidase from E. coli, immobilised on tresyl agarose (see Example 3C). The glycosidase was dissolved in 105 ml buffer (see Example 10A) and 45 ml DMF. β-galactosidase agarose (0.2 g, 300 units) was added, and the reaction was allowed to continue for 4 days at room temperature under gentle agitation. The products were isolated and analysed in accordance with Example 10A. The yield of Gal(β1-3)Gal(β)-OMe, recrystallised from MeOH, was 4 g (29%) and of Gal(β1-6)Gal(β)-OMe 400 mg (3%).

EXAMPLE 11

Preparation of Gal(β1-6)Gal(α)-OMe

This test was analogous to Example 10A, but use was made of 2.7 g Gal(β)-OPhNO2-o, 5 g Gal(β)-OMe and 1.0 mg β-galactosidase from E. coli (see Example 10A) dissolved in 35 ml buffer (see Example 10A) and 15 ml DMF. After reaction at room temperature for 5 hours, the product was isolated and analysed in accordance with Example 10. The yield of crystalline Gal(β1-6)Gal(β)-OMe was 450 mg. Other isomers were formed in negligible amounts.

EXAMPLE 12

One-vessel synthesis of
Gal($\beta$1-3)Gal-OCH$_2$CH$_2$OC(O)C(CH$_3$)=CH$_2$ and
Gal($\beta$)-OCH$_2$CH$_2$OC(O)C(CH$_3$)=CH$_2$ This Example demonstrates in situ preparation of the acceptor glycoside. 18 g lactose were dissolved in a mixture of 160 ml buffer (see Example 10), 75 ml DMF and 15 ml hydroxyethyl methacrylate. $\beta$-galactosidase-agarose (1.5 g, 2250 units, see Example 10B) was added, and the reaction was allowed to continue at room temperature under gentle agitation. After 6 days, the immobilised enzyme was filtered off, and the products were isolated by column chromatography. 2.6 g Gal($\beta$)-OCH$_2$CH$_2$OC(O)C(CH$_3$)=CH$_2$ and 160 mg Gal($\beta$1-3)GalOCH$_2$CH$_2$OC(O)C(CH$_3$)=CH$_2$ were obtained.

EXAMPLE 13

Synthesis of Gal($\beta$1-3)GlcNAc($\beta$)-OCH$_2$CH$_2$Si(Me)$_3$ 6 g Gal($\beta$)-OPhNO$_2$-o and 1 g GlcNAc($\beta$)-O(CH$_2$)$_2$-Si(CH$_3$)$_3$ were suspended in 30 ml 0.1M sodium phosphate (pH 7.0) containing the supernatant of an extract obtained from 10 g bovine testes. The reaction was allowed to continue for 2 days at 40° C. The reaction was terminated and the products were isolated by column chromatography in accordance with Example 10A. The yield of Gal($\beta$1-3)-GlcNAc-($\beta$)-O-(CH$_2$)$_2$Si(CH$_3$)$_3$ was 200 mg after deacetylation.

EXAMPLE 14

Synthesis of GlcNAc($\beta$1-6)Man($\beta$)-OMe 3 g GlcNAc($\beta$)-OPhNO$_2$-p (p-nitrophenyl-N-acetyl-$\beta$-D-glucosaminide) and 16 g Man($\alpha$)-OMe were dissolved in 88 ml buffer (see Example 1A) and 12 ml DMF. N-acetyl-$\beta$-D-glucosaminidase (jack bean; EC 3.2.1.30; 20 units, 0.3 ml, Sigma Laboratories) were added, and the reaction was allowed to continue for 3 days at room temperature. The reaction was terminated, and the product was isolated and analysed in accordance with Example 1A. The yield of pure crystalline GlcNAc($\beta$1-6)Man($\alpha$)-OMe was 350 mg.

EXAMPLE 15

Synthesis of Fuc($\alpha$1-3)Gal($\alpha$)-OMe 0.31 g p-nitrophenyl-$\alpha$-L-fucopyranoside (Fuc-($\alpha$)OPhNO$_2$) and 3 g Gal($\alpha$)-OMe were dissolved in 25 ml buffer (0.05M sodium phosphate, pH 6.2). $\alpha$-L-fucosidase (bovine kidney; EC 3.2.1.51; 0.3 ml, 1 unit, Sigma Laboratories) was added, and the reaction was allowed to continue at 37° C. for 2 days. The reaction was interrupted, and the product was isolated and analysed in accordance with Example 1A. The yield of peracetylated Fuc($\alpha$1-3)Gal($\alpha$)-OMe was 35 mg.

I claim:

1. A method of controlling the regioselectivity of the glycosidic bond formed between glycosyl donor and glycosyl acceptor in the enzymatic production of an oligosaccharide compound which either consists of or is a fragment or an analog of the carbohydrate part in a glycoconjugate, synthesized by reverse hydrolysis or transglycosidation, comprising reacting a donor substance which is a monosaccharide or oligosaccharide or a glycoside of a monosaccharide or oligosaccharide, with an acceptor substance which is an O-, N-, C- or S-glycoside consisting of a monosaccharide, oligosaccharide or a saccharide analog and at least one aglycon which is O-, N-, C- or S-glycosidically bonded in 1-position, in the presence of an exo- or endoglycosidase of EC group 3.2, the $\alpha$- or $\beta$-configuration being selected on the glycoside bond between the glycosyl group and the aglycon in the acceptor substance, and separating the oligosaccharide compound from the reaction mixture.

2. A method as claimed in claim 1, wherein the carbohydrate portion of the donor and acceptor substance includes one or more of the monosaccharides L-fucose, D-galactose, D-mannose, N-acetyl neuraminic acid, N-acetyl-D-galactosamine, and N-acetyl-D-glucosamine.

3. A method as claimed in claim 1, wherein the acceptor substance includes an analog of any of the monosaccharides L-fucose, D-galactose, D-mannose, N-acetyl-D-galactosamine and N-acetyl-D-glucosamine.

4. A method as claimed in claim 1 wherein the aglycon is an aliphatic or aromatic substance.

5. A method as claimed in claim 4, wherein the aglycon is a glycosidically bonded methyl, CH$_3$(CH$_2$)$_n$ where n=$\geq$1, phenyl, p-nitrophenyl, o-nitrophenyl, 2-bromoethyl, trimethylsilyl ethyl or an CH$_2$=C(CH$_3$)—C(O)—OCH$_2$CH$_2$ group.

6. A method as claimed in claim 1 wherein the aglycon is a fluorogenic substance.

7. A method as claimed in claim 1 wherein the aglycon is an amino, nitrile or amide group or contains such a group.

8. A method as claimed in claim 1, wherein the aglycon contains a phosphate, sulphate or carboxyl group, or a derivative thereof.

9. A method as claimed in claim 1, wherein the aglycon is an organic substance which, directly or after chemical modification, can be bonded covalently to lipids, peptides, proteins, enzymes or to carrier materials used in affinity distribution systems, affinity chromatography, diagnostics or therapy.

10. A method as claimed in claim 1, wherein the aglycon is polymerizable.

11. A method as claimed in claim 1, wherein the aglycon is an amino acid, peptide, lipid, or a derivative or an analog thereof.

12. A method as claimed in claim 1 wherein the donor is lactose, raffinose, chitobiose or dimannoside.

13. A method as claimed in claim 1 wherein the donor substance is a mono- or oligosaccharide with an $\alpha$- or $\beta$-glycosidically bonded organic substance.

14. A method as claimed in claim 13, wherein the organic substance is a methyl, CH$_3$(CH$_2$)$_n$, wherein n=$\geq$1, phenyl, p-nitrophenyl, o-nitrophenyl, or 4-methylumbelliferyl group.

15. A method as claimed in claim 1 wherein the enzyme is a galactosidase, mannosidase, N-acetylhexosaminidase, N-acetylgalactoseaminidase, N-acetyl glucoseaminidase or a fucosidase.

16. A method as claimed in claim 1 wherein the enzyme employed is thermostable.

17. A method as claimed in claim 1 wherein the enzyme is used in situ or after first having been isolated completely or partly from its natural biological environment.

18. A method as claimed in claim 1 wherein the enzyme is in crystalline form.

19. A method as claimed in claim 1, wherein the enzyme is enclosed in micelles.

20. A method as claimed in claim 1 wherein the enzyme is covalently modified with an organic substance.

21. A method as claimed in claim 1, wherein the enzyme is immobilized via precipitation, adsorption, enclosure, chelation or covalent bonding, to a polymeric substance or derivative thereof which is insoluble in protic or aprotic solvents.

22. A method as claimed in claim 1, wherein the polymeric substance consists of agarose, cellulose, silica, polyacrylicamide, or polyacrylate-based plastics.

23. A method as claimed in claim 1 wherein an oligosaccharide compound having biospecific affinity to another substance is synthesized and isolated.

* * * * *